United States Patent [19]

Bittler et al.

[11] Patent Number: 4,472,310
[45] Date of Patent: Sep. 18, 1984

[54] 5β-HYDROXY-Δ⁶-STEROIDS AND PROCESS FOR THE PREPARATION THEREOF

[75] Inventors: Dieter Bittler; Henry Laurent; Klaus Nickisch; Robert Nickolson; Rudolf Wiechert, all of Berlin, Fed. Rep. of Germany

[73] Assignee: Schering Aktiengesellschaft, Berlin, Fed. Rep. of Germany

[21] Appl. No.: 359,713

[22] PCT Filed: Jul. 2, 1981

[86] PCT No.: PCT/DE81/00111
§ 371 Date: Mar. 11, 1982
§ 102(e) Date: Mar. 11, 1982

[87] PCT Pub. No.: WO82/00294
PCT Pub. Date: Feb. 4, 1982

[30] Foreign Application Priority Data

Jul. 11, 1980 [DE] Fed. Rep. of Germany ....... 3026783

[51] Int. Cl.³ .............................................. C07J 21/00
[52] U.S. Cl. ............................ 260/239.57; 260/397.4; 260/397.5; 260/239.55 C; 260/397
[58] Field of Search .................. 260/239.55, 239.55 C, 260/239.57, 397.1, 397.4, 397.5

[56] References Cited

U.S. PATENT DOCUMENTS

| | | | |
|---|---|---|---|
| 3,798,213 | 3/1974 | Arth | 260/239.57 |
| 3,883,512 | 5/1975 | Stache et al. | 260/239.57 |
| 3,890,304 | 6/1975 | Weier | 260/239.57 |
| 3,966,714 | 6/1976 | Philippson | 260/239.57 |
| 4,119,627 | 10/1978 | Wieland | 260/239.57 |

OTHER PUBLICATIONS

Helv. Chim. Acta., vol. 62, (1979), No. 7, p. 2277 relied on, Article by Wieland.
Steroids 21:47–61, (1973).

Primary Examiner—Elbert L. Roberts
Attorney, Agent, or Firm—Millen & White

[57] ABSTRACT

The disclosure concerns 5β-hydroxy-Δ⁶-steroids of the general formula

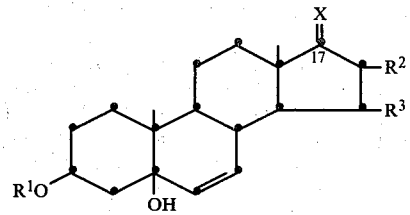

wherein
R¹ is hydrogen, acyl, lower alkyl, or the tetrahydropyranyl residue and
R², R³ individually are respectively hydrogen or jointly are methylene and
X stands for oxygen, the groupings

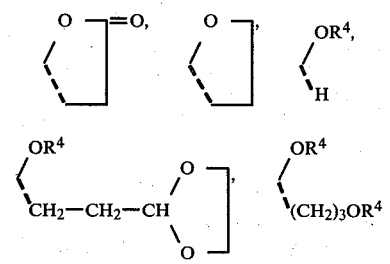

(wherein R⁴ means hydrogen or acyl) and

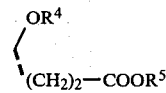

(wherein R⁵ means hydrogen or lower alkyl) and a process for the preparation thereof by reacting corresponding 7α-chloro-5β,6β-epoxy steroids in an inert solvent with metallic zinc in a lower aliphatic carboxylic acid or dilute mineral acid at temperatures of between room temperature and 100° C., preferably at 40°–70° C.

The compounds producible by this method are intermediates for the preparation of 3-keto-Δ⁴-6β,7β-methylene steroids constituting pharmacologically valuable compounds, for example aldosterone antagonists.

5 Claims, No Drawings

5β-HYDROXY-Δ⁶-STEROIDS AND PROCESS FOR THE PREPARATION THEREOF

BACKGROUND OF THE INVENTION

The invention relates to the subject matter of the claims.

It is known that 3β-acetoxy-5-hydroxy-5β,17α-pregn-6-ene-21,17-carbolactone can be prepared from 3β-acetoxy-5,6β-epoxy-5β-pregnane-21,17-carbolactone via the intermediate stage of 3β-acetoxy-5-hydroxy-6α-phenylseleno-5β-pregnane-17,21-carbolactone [Helv. Chim. Acta 62: 2276(1976)].

This process has the disadvantage, however, that highly toxic organoselenium compounds, such as, for example, diphenyldiselenide, are required for the synthesis, the handling of these compounds presenting difficulties on an industrial scale; disposal of the wastes of these compounds can only be made in special dumps, and furthermore these compounds are not likely to be available as a raw material in abundant amounts.

SUMMARY OF THE INVENTION

It is, therefore, an object of the present invention to provide a way for producing 5β-hydroxy-Δ⁶-steriods without the use of selenium.

This object has been attained by the process as characterized in the claims.

DETAILED DISCUSSION

Acyl is understood to mean acid residues of up to 12 carbon atoms and derived from acids customarily used in steroid chemistry for esterifications. Preferred acids are carboxylic acids of 1–8 carbon atoms. The carboxylic acids can also be branched, polybasic, or substituted in the usual way, for example by a hydroxy or amino group. Also suitable are cycloaliphatic, aromatic, mixed aromatic-aliphatic, or heterocyclic acids. Preferred acids for the formation of the acylresidue are, for example, acetic acid, propionic acid, caproic acide, trimethylacetic acid, cyclopentylpropionic acid, cyclohexylacetic acid, phenylpropionic acid, phenylacetic acid, dialkylaminoacetic acid, piperidinoacetic acid, succinic acid, and benzoic acid.

Alkyl is understood to mean residues derived from aliphatic hydrocarbons and exhibiting 1–6 carbon atoms, such as, for example, methyl, ethyl, propyl, isopropyl, n-butyl, isobutyl, and tert.-butyl.

The compounds producible according to the invention are intermediates for the preparation of 3-keto-Δ⁴-6β,7β-methylene steroids representing pharmacologically valuable compounds.

The process of this invention is conducted by dissolving the 7α-chloro-5β,6β-epoxy steroid in an inert protonic solvent and stirring the solution with metallic zinc, for example in pulverized or granular form or in the form of filings, in the presence of an aliphatic carboxylic acid or a dilute mineral acid at between room temperature and about 100° C.

Suitable inert protonic solvents are all those which do not react with the reactants. Examples are aliphatic alcohols, such as methanol, ethanol, n-propanol, and isopropyl alcohol; aliphatic and cycloaliphatic ethers, such as diisopropyl ether, tetrahydrofuran, and dioxane, as well as water.

Besides acetic acid, which is preferably employed, formic acid and propionic acid are likewise suitable as aliphatic carboxylic acids for conducting the reaction of the invention. However, the use of a dilute mineral acid is also possible, such as hydrochloric acid or sulfuric acid.

The acid utilized is employed in excess. The excess amount is 30–100 times the quantity (mol equivalents). The acid is suitably used in a concentration of 0.2–1.0 mole/liter.

The reaction mixture is heated, a temperature range of 40°–70° C. being preferred.

The duration of the reaction is about 0.5–7 hours, this time being dependent on the starting material employed and especially on the temperature.

The course of the reaction according to the invention was surprising since, under the reaction conditions applied (acidic, temperature above room temperature), it would have to be expected that the thus-formed 5β-hydroxy-Δ⁶- steroids would be converted by allyl rearrangement into corresponding secondary products. For it is known from the work performed by Morand [P. Morand and A. van Tongerloo, Steroids 21: 47-61 (1973)] that 5-hydroxy-Δ⁶-steroids are converted even at room temperature, in the presence of 80% acetic acid, into the corresponding allyl rearrangement products, such as 7-hydroxy- and 7-acetoxy-Δ⁵-steroids. Moreover, it is known from this work that, in part, even polyenes are formed when heating 5-hydroxy-Δ⁶-steroids with 80% acetic acid.

Using the intermediate product prepared according to this invention, 3β-acetoxy-5-hydroxy-15β,16β-methylene-5β-androst-6-en-17-one, the conventional 6β,7β;15β,16β-dimethylene-3-oxo-17α-pregn-4-ene-21,17-carbolactone, which has an aldosterone-antagonistic effect, can be prepared, for example, in the following way:

A solution of 3β-acetoxy-5-hydroxy-15β,16β-methylene-5β-androst-6-en-17-one in 300 ml of methanol is stirred with 15 g of potassium carbonate for 30 minutes at room temperature. The reaction solution is diluted with diethyl ether, washed with water, dried, and evaporated, thus obtaining 27 g of 3β,5-dihydroxy-15β,16β-methylene-5β-androst-6-en-17-one, mp 187°–190° C., (acetone).

A solution of 26 g of 3β,5-dihydroxy-15β,16β-methylene-5β-androst-6-en-17-one in 520 ml of ethylene glycol dimethyl ether is stirred with 78 g of zinc-copper and 69 ml of methylene iodide for 4 hours at 80° C. The mixture is then diluted with methylene chloride, washed with saturated ammonium chloride solution and water, dried, and evaporated. The residue is chromatographed on silica gel, thus obtaining 16.3 g of 3β,5-dihydroxy-6β,7β;15β,16β-dimethylene-5β-androstan-17-one, mp 205.5°–207° C.

A solution is prepared from 25.1 g of 3β,5-dihydroxy-6β,7β;15β,16β-dimethylene-5β-androstan-17-one and 500 ml of tetrahydrofuran. Under cooling to 0° C. and an argon atmosphere, 75.5 g of potassium methylate is added to this solution and the latter is then combined dropwise under agitation with 50.4 ml of propargyl alcohol dissolved in 104 ml of tetrahydrofuran. The reaction mixture is stirred at 0° C. for 20 hours and poured into ice water. After neutralizing with dilute sulfuric acid, the thus-obtained precipitate is filtered off and dried. The crude product is chromatographed on silica gel, thus obtaining 25 g of 17α-(3-hydroxy-1-propynyl)-6β,7β;15β,16β-dimethylene-5β-androstane-3β,5,15β-triol, mp 202°–203° C. (acetone).

24.5 g of 17α-(3-hydroxy-1-propynyl)-6β,7β;15β,16β-dimethylene-5β-androstane-3β,5,17β-triol is hydrogenated in 250 ml of tetrahydrofuran and 125 ml of methanol in the presence of 3.75 g of palladium on carbon (10%) and 0.5 ml of pyridine until 2 equivalents of hydrogen have been absorbed. The mixture is filtered off from the catalyst and evaporated, thus producing 24.7 g of 17α-(3-hydroxypropyl)6β,7β;15β,16β-dimethylene-5β-androstane-3β,5,17β-triol which is used in the subsequent stage without further purification.

A solution of 24.7 g of 17α-(3-hydroxypropyl)6β,7β;15β,16β-dimethylene-5β-androstane-3β,5,17β-triol in 247 ml of pyridine is combined with a solution of 74.1 g of chromium (VI) oxide in 247 ml of water and 494 ml of pyridine and stirred for 16 hours at 50° C. Thereafter the mixture is diluted with methylene chloride, washed with water, dried, and evaporated. The residue is chromatographed on silica gel. Recrystallization from diisopropyl ether-acetone yields 14.5 g of 6β,7β;15β,16β-dimethylene3-oxo-17α-pregn-4-ene-21,17-carbolactone, mp 196.5°-197.5° C.

UV: $\epsilon_{265} = 18,700$ (methanol).

Starting with 3β,5-dihydroxy-15β,16β-methylene5β,17α-pregn-6-ene-21,17-carbolactone as the intermediate prepared according to the invention, the same 6β,7β;15β,16β-dimethylene-3-oxo-17α-pregn-4-ene-21,17-carbolactone is obtained, for example, by the following method:

A solution is prepared from 5 g of 3β,5-dihydroxy-15β,16β-methylene-5β,17α-pregn-6-ene-21,17-carbolactone and 100 ml of tetrahydrofuran and combined with 15 g of zinc-copper. Within 7 hours, 13.2 ml of methylene iodide is added dropwise to the mixture in such a way that the temperature does not rise above 30° C., and the mixture is agitated for another 10 hours at room temperature. To remove the metal, the mixture is filtered over "Celite", the filtrate is diluted with methylene chloride and washed with saturated ammonium chloride solution, dried over magnesium sulfate, and evaporated under vacuum. The residue is chromatographed on silica gel, thus obtaining 4.4 g of 3β,5-dihydroxy-6β,7β;15β,16β-dimethylene-5β,17α-pregnane-21,17-carbolactone as an oil.

A solution is prepared from 2.8 g of 3β,5-dihydroxy-6β,7β;15β,16β-dimethylene-5β,17α-pregnane-21,17-carbolactone and 28 ml of pyridine and combined with a solution of 15 g of chromium(VI) oxide in 28 ml of pyridine and 14 ml of water. The mixture is stirred for 16 hours at 50° C. After cooling, the mixture is diluted with methylene chloride, washed with water, dried over magnesium sulfate, and concentrated under vacuum. The residue is chromatographed on silica gel, thus obtaining 2.3 g of 6β,7β;15β,16β-dimethylene-3-oxo-17α-pregn-4-ene-21,17-carbolactone, mp 198°-198.5° C.

The following examples are to explain the process of this invention.

EXAMPLE 1

A solution of 21 g of 3β-acetoxy-7α-chloro-5β,6β-epoxy-17,17-ethylenedioxy-15β,16β-methylene-5β-androstane in 105 ml of tetrahydrofuran, 105 ml of acetic acid, and 27 ml of water is combined with 63 g of zinc dust and stirred for 1.5 hours at 80° C. The mixture is then decanted off from the zinc, washed with methylene chloride, and the organic phase is washed with sodium bicarbonate solution and water. After drying and evaporation, the residue is chromatographed on silica gel, thus obtaining 13.8 g of 3β-acetoxy-5-hydroxy-15,16β-methylene-5β-androst-6-en-17-one, mp 191°-194° C.

The starting material was produced as follows:

(A) A solution of 95 g of 3β-hydroxy-15β,16β-methylene-5-androsten-17-one in 190 ml of pyridine was combined with 95 ml of acetic anhydride and stirred for 1.5 hours at 95° C. The precipitate obtained after pouring the mixture into ice water was filtered off, washed thoroughly with water, and dried, thus obtaining 107 g of 3β-acetoxy-15β,16β-methylene-5-androsten-17-one as a crude product. A sample extracted by boiling with diisopropyl ether melted at 140.5°-141° C.

(B) A solution of 105 g of 3β-acetoxy-15β,16β-methylene-5-androsten-17-one in 1.05 l of methylene chloride was combined with 315 ml of ethylene glycol, 210 ml of triethyl orthoformate, and 10.5 g of p-toluenesulfonic acid and agitated for 1 hour at room temperature. The reaction solution was combined with 40 ml of pyridine and diluted with ether, then washed with water, dried, and evaporated. The residue was triturated with pentane and vacuum-filtered, thus producing 109 mg of 3β-acetoxy-17,17-ethylenedioxy-15β,16β-methylene-5-androstene, mp 177°-178.5° C.

(C) Under agitation, 600 ml of methylene chloride, cooled to −20° C., was combined in succession with 81 g of chromium(VI) oxide, dried over phosphorus pentoxide, and 84 g of 3,5-dimethylpyrazole. The mixture was stirred for 30 minutes, combined with 23.2 g of 3β-acetoxy-17,17-ethylenedioxy-15β,16β-methylene-5-androstane, and stirred for 4 hours at −10° C. Subsequently, the reaction solution was combined with 342 ml of 5N sodium hydroxide solution, stirred for 1 hour at 0° C., combined with 120 ml of diethyl ether, and stirred for another 30 minutes. The aqueous phase was separated and the organic phase washed with water, dried, and evaporated. The residue was chromatographed on silica gel, thus producing 17.2 g of 3β-acetoxy-17,17-ethylenedioxy-15β,16β-methylene-5-androsten-7-one, mp 193°-197° C.

(D) 31 g of 3β-acetoxy-17,17-ethylenedioxy-15β,16β-methylene-5-androsten-7-one was reacted at room temperature within 1.5 hours in 310 ml of tetrahydrofuran with 31 g of lithium tri-tert.-butoxyaluminohydride. The reaction solution was diluted with diethyl ether, washed with potassium-sodium tartrate solution and water, dried, and evaporated. The residue was chromatographed on silica gel, thus obtaining 24.3 g 3β-acetoxy-17,17-ethylenedioxy-15β,16β-methylene-5-androsten-7β-ol, mp 199.5°-200° C. (acetone).

(E) A solution of 23.3 g of 3β-acetoxy-17,17-ethylenedioxy-15β,16β-methylene-5-androsten-7β-ol in 350 ml of toluene was combined dropwise, after adding vanadium(IV) oxide acetylacetonate, within 35 minutes with 23.3 ml of 80% tert.-butyl hydroperoxide, dissolved in 115 ml of toluene. The reaction solution was maintained at 80° C. for another 30 minutes, then cooled, diluted with diethyl ether, washed with sodium bisulfite solution, sodium bicarbonate solution, and water, and dried and evaporated, thus obtaining 24.5 g of 3β-acetoxy-5,6β-epoxy-17,17-ethylenedioxy-15β,16β-methylene-5β-androstan-7β-ol, mp 162°-163° C. (diisopropyl ether).

(F) A solution of 24 g of 3β-acetoxy-5,6β-epoxy-17,17-ethylenedioxy-15β,16β-methylene-5β-androstan-7β-ol in 48 ml of pyridine and 48 ml of carbon tetrachloride was combined with 28 g of triphenylphosphine and stirred for 1.5 hours at room temperature. The reaction mixture was diluted with methylene chloride, washed with water, dried, and evaporated. The residue was chromatographed on silica gel, thus producing 21.5 g of 3β-acetoxy-7α-chloro-5,6β-epoxy-17,17-ethylenedioxy-15β,16β-methylene-5β-androstane, mp 169°–170° C. (diisopropyl ether).

EXAMPLE 2

200 mg of 17β-acetoxy-3β-benzoyloxy-7α-chloro-5,6β-epoxy-15β,16β-methylene-5β-androstane is stirred in 4 ml of acetic acid and 4 ml of propan-2-ol with 800 mg of zinc dust for 1 hour at 80° C. The mixture is filtered off from the zinc, washed with diethyl ether, and worked up analogously to Example 1. After chromatography and recrystallization from diisopropyl ether-acetone, 135 mg of 17β-acetoxy-3β-benzoyloxy-15β,16β-methylene-5β-androst-6-en-5-ol is obtained, mp 212°–212.5° C.

Preparation of starting material (A) A solution of 5.0 g of 3β-hydroxy-15β,16β-methylene-5-androsten-17-one in 50 ml of pyridine was combined under ice cooling with 5 ml of benzoyl chloride and then stirred for 17 hours at room temperature. After the addition of 10 ml of water, the mixture was stirred for another hour; then the reaction solution was diluted with methylene chloride and washed with sodium carbonate solution and water. After drying and evaporation, the residue was triturated with diisopropyl ether and vacuum-filtered, thus obtaining 6.4 g of 3β-benzoyloxy-15β,16β-methylene-5-androsten-17-one, mp 250°–258° C.

(B) 6.4 g of 3β-benzoyloxy-15β,16β-methylene-5-androsten-17-one was stirred in 64 ml of tetrahydrofuran with 6.4 g of lithium tri-tert.-butoxyaluminohydride for 1 hour at room temperature. The solution was then diluted with ether, washed with 2N sulfuric acid and water, dried, and evaporated, yielding as the residue 6.5 g of 3β-benzoyloxy-15β,16β-methylene-5-androsten-17β-ol, used without further purification in the subsequent stage.

(C) 6.5 g of 3β-benzoyloxy-15β,16β-methylene-5-androsten-17β-ol, 13 ml of acetic anhydride, and 26 ml of pyridine were heated for 1.5 hours to 95° C. After ice water precipitation, the sediment was filtered off and taken up in methylene chloride. The solution was washed with water, dried, and evaporated, thus obtaining 6.9 g of crude 17β-acetoxy-3β-benzoyloxy-15β,16β-methylene-5-androstene, used without further purification in the next stage.

(D) 6.9 g of 17β-acetoxy-3β-benzoyloxy-15β,16β-methylene-5-androstene was combined with 69 ml of carbon tetrachloride with an acetic tert.-butyl chromate solution prepared from 10.35 g of chromium(VI) oxide, 90 ml of carbon tetrachloride, 28.2 ml of tert.-butyl alcohol, 37.2 ml of acetic acid, and 134 ml of acetic anhydride. The reaction solution was then stirred for 32 hours at 80° C., diluted with methylene chloride, and washed with sodium acetate solution, sodium bicarbonate solution, and water. After drying and evaporation, the resultant residue was chromatographed on silica gel, thus obtaining 4.4 g of 17β-acetoxy-3β-benzoyloxy-15β,16β-methylene-5-androsten-7-one, mp 245°–246° C. (acetone-diisopropyl ether).

(E) The thus-produced 7-ketone, analogously as described in Example 1 in connection with the preparation of the starting material in stages (D)–(F), was reduced with lithium tri-tert.-butoxyaluminohydride to the 17β-acetoxy-3β-benzoyloxy-15β,16β-methylene-5-androsten-7β-ol, epoxidized with tert.-butyl hydroperoxide in the presence of vanadium(IV) oxide acetylacetonate to 17β-acetoxy-3β-benzoyloxy-5,6β-epoxy-15β,16β-methylene-5β-androstan-7β-ol, and then reacted with triphenylphosphine in carbon tetrachloride and pyridine to the 17β-acetoxy-3β-benzoyloxy-7α-chloro-5,6β-epoxy-15β,16β-methylene-5β-androstane, mp 201.5°–206° C. (diisopropyl ether-acetone).

EXAMPLE 3

Analogously to Example 2, 13.5 g of 3β,17β-dibenzoyloxy-7α-chloro-5,6β-epoxy-15β,16β-methylene-5β-androstane is reacted in 130 ml of acetic acid and 130 ml of propan-2-ol with 49.5 g of zinc dust and worked up. Chromatography on silica gel yields 8.8 g of 3β,17β-dibenzoyloxy-15β,16β-methylene-5β-androst-6-en-5-ol, mp 223°–225° C. (acetone-diisopropyl ether).

Preparation of starting material (A) A solution of 21 g of 3β-hydroxy-15β,16β-methylene-5-androsten-18-one in 210 ml of tetrahydrofuran was stirred with 21 g of lithium tri-tert.-butoxyaluminohydride for 1 hour at room temperature. The mixture was then diluted with diethyl ether, washed with 2N sulfuric acid and water, dired, and evaporated, thus obtaining 19 g of 15β,16β-methylene-5-androstene-3β,17β-diol, used without further purification in the subsequent stage.

(B) 15β,16β-Methylene-5-androstene-3β,17β-diol, analogously to Example 2, as described in the preparation of the starting material, was reacted with benzoyl chloride to 3β,17β-dibenzoyloxy-15β,16β-methylene-5-androstene, oxidized with tert.-butyl chromate to 3β,17β-dibenzoyloxy-15β,16β-methylene-5-androsten-7-one, and reduced with lithium tri-tert.-butoxyaluminohydride to 3β,17β-dibenzoyloxy-15β,16β-methylene-5-androsten-7β-ol; the last-mentioned compound was reacted with tert.-butyl hydroperoxide to 3β,17β-dibenzoyloxy-5,6β-epoxy-15β,16β-methylene-5β-androstane and converted with triphenylphosphine in carbon tetrachloride and pyridine into 3β,17β-dibenzoyloxy-7α-chloro-5,6β-epoxy-15β,16β-methylene-5β-androstane. The product obtained after chromatography and recrystallization from diisopropyl ether-acetone melted at 197.5°–198.5° C.

EXAMPLE 4

3.0 g of 17β-acetoxy-3β-benzoyloxy-7α-chloro-5,6β-epoxy-5β-androstane is reacted analogously to Example 2 in 30 ml of acetic acid and 30 ml of propan-2-ol with 9 g of zinc dust and worked up. Yield: 2.8 g of 17β-acetoxy-3β-benzoyloxy-5β-androst-6-en-5-ol, mp 180°–185° C.

Preparation of starting material

Analogously to Example 2(A)–(C), 3β-hydroxy-5-androsten-17-one was converted into 17β-acetoxy-3β-benzoyloxy-5-androstene. Analogously to Example 2(D), 17β-acetoxy-3β-benzoyloxy-5-androsten-7-one was produced from this product with tert.-butyl chromate. Reducing, epoxidizing, and chlorination reactions were carried out analogously to Example 1(D)–(F), thus obtaining 17β-acetoxy-3β-benzoyloxy-7α-chloro-5,6β-epoxy-5β-androstane, mp 173°–175.5° C. after chromatography on silica gel.

EXAMPLE 5

300 mg of 3β-acetoxy-7α-chloro-5,6β-epoxy-15β,16β-methylene-5β,17α-pregnane-21,17-carbolactone is stirred in 15 ml of propan-2-ol and 15 ml of acetic acid with 900 mg of zinc dust for 2 hours at 80° C. After filtration, the mixture is diluted with methylene chloride and washed with sodium bicarbonate solution and water, dried over magnesium sulfate, and evaporated under vacuum. The residue is purified by preparative thin-layer chromatography, yielding 150 mg of 3β-acetoxy-5-hydroxy-5β,17α-pregn-6-ene-21.17-carbolactone, mp 209°–211° C.

Preparation of starting material (A) A suspension of 20 g of 3β-hydroxy-15β,16β-methylene-5-androsten-17-one in 400 ml of benzene was dried azeotropically by removing 40 ml of liquid by distillation, and combined at room temperature with 50 ml of distilled dihydropyran and 250 ml of toluenesulfonic acid. After 1 hour at room temperature, 4 ml of pyridine was added, the mixture was diluted with diethyl ether, washed with sodium bicarbonate solution and water, and dried over magnesium sulfate. The crude product obtained after evaporation was extracted by boiling with methanol, filtered, and dried, yielding 22.4 g of 15β,16β-methylene-3β-(tetrahydropyran-2-yloxy)-5-androsten-17-one, mp 175°–178° C.

(B) 22 g of 15β,16β-methylene-3β-(tetrahydropyran-2-yloxy)-5-androsten-17-one was dissolved in 400 ml of tetrahydrofuran; under ice cooling and an argon atmosphere, 65 g of potassium ethylate was added and under agitation a solution of 44 ml of propargyl alcohol in 88 ml of tetrahydrofuran was added dropwise to this suspension. The mixture was then stirred under argon for 4 hours at room temperature. This solution was poured into 5 l of saturated sodium chloride solution and neutralized with acetic acid. The precipitate was filtered off and taken up in methylene chloride. The solution was washed, dried, and evaporated. The resultant crude product was triturated with ethyl acetate, thus obtaining 23 g of 17α-(3-hydroxy-1-propynyl)-15β,16β-methylene-3β-(tetrahydropyran-2-yloxy)-5-androsten-17β-ol, mp 193°–196° C.

(C) A solution of 22 g of 17α-(3-hydroxy-1-propynyl)-15β,16β-methylene-3β-(tetrahydropyran-2-yloxy)-5-androsten-17β-ol in 1.3 l of methanol was combined with 3 spoonfuls of Raney nickel and shaken under a hydrogen atmosphere, during which step 2.27 l of hydrogen was absorbed. The catalyst was then vacuum-filtered, the filtrate evaporated under vacuum, and the residue recrystallized from ethyl acetate, thus obtaining 16.75 g of 17α-(3-hydroxypropyl)-15β,16β-methylene-3β-(tetrahydropyran-2-yloxy)-5-androsten-17β-ol, mp 156°–160° C.

(D) A solution of 15 g of 17α-(3-hydroxypropyl)-15β,16β-methylene-3β-(tetrahydropyran-2-yloxy)-5-androsten-17β-ol in 1.2 l of dimethylformamide was combined with 48 g of pyridinium dichromate and stirred for 3 hours at room temperature. The mixture was then poured into saturated sodium chloride solution, the precipitate was filtered off and washed with methanol. The resultant crude product was recrystallized from methanol, thus obtaining 14.3 g of 3β-(tetrahydropyran-2-yloxy)-15β,16β-methylene-17α-pregn-5-ene-21,17-carbolactone, mp 218°–220° C.

(E) 14.3 g of 3β-(tetrahydropyran-2-yloxy)-15β,16β-methylene-17α-pregn-5-ene-21,17-carbolactone was dissolved in 250 ml of methanol and 150 ml of methylene chloride, 2 ml of 3N hydrochloric acid was added thereto, and the mixture was stirred for 2 hours at room temperature. Then the mixture was evaporated under vacuum, the residue dissolved in methylene chloride and washed neutral. The crude product, thus formed after evaporation, was extracted by boiling with methanol, thus obtaining 11.6 g of 3β-hydroxy-15β,16β-methylene-17α-pregn-5-ene-21,17-carbolactone, mp 216°–223° C.

(F) 750 mg of 3β-hydroxy-15β,16β-methylene-17α-pregn-5-ene-21,17-carbolactone was dissolved in 10 ml of pyridine, combined with 10 ml of acetic anhydride, and heated for 1 hour on a steam bath. The mixture was then introduced into ice water, the precipitate filtered off and dried under vacuum. The resultant crude product was purified by gradient chromatography, thus obtaining 683 mg of 3β-acetoxy-15β,16β-methylene-17α-pregn-5-ene-21,17-carbolactone, mp 224°–226° C.

(G) The thus-produced 3β-acetoxy-15β,16β-methylene-17α-pregn-5-ene-21,17-carbolactone was converted analogously to Example 1(C)–(F) into 3β-acetoxy-7α-chloro-5,6-epoxy-15β,16β-methylene-5β,7α-pregnane-21,17-carbolactone.

EXAMPLE 6

A suspension is prepared from 61 g of 3β-(tetrahydropyran-2-yloxy)-7α-chloro-5,6β-epoxy-15β,16β-methylene-5β,17α-pregnane-21,17-carbolactone in 400 ml of tetrahydrofuran, 400 ml of acetic acid, and 160 ml of water. The suspension is combined within 45 minutes with 150 g of zinc dust in 3 portions and heated for 4.5 hours to 70° C. After cooling, the mixture is stirred into ice water, neutralized with sodium bicarbonate, and extracted with methylene chloride. The extract is dried, after washing with water, over magnesium sulfate and evaporated under vacuum. The residue is chromatographed on silica gel, thus obtaining 37.9 g of 3β,5-dihydroxy-15β,16β-methylene-5β,17α-pregn-6-ene-21,17-carbolactone, mp 237°–238° C.

Preparation of starting material

Analogously to Example 1(C)–(F), 3β-(tetrahydropyran-2-yloxy)-15β,16β-methylene-17α-pregn-5-ene-21,17-carbolactone was converted into 3β-(tetrahydropyran-2-yloxy)-7α-chloro-5,6β-epoxy-15β,16β-methylene-5β,17α-pregnane-b 21,17-carbolactone.

What is claimed is:

1. A process for preparing a 5β-hydroxy-Δ⁶-steroid of the general formula

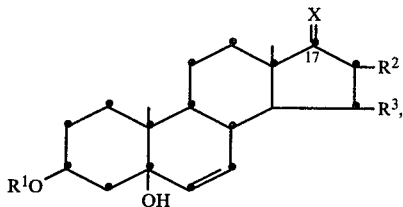

wherein
  $R^1$ is hydrogen, acyl, lower alkyl, or tetrahydropyranyl and
  $R^2$, $R^3$ jointly are methylene and
  X is oxygen, or

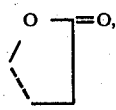

comprising treating the corresponding 7α-chloro-5β,6β-epoxy steroid with a lower aliphatic carboxylic acid or a dilute mineral acid, in an inert solvent, in the presence of metallic zinc at a temperature of between room temperature and 100° C.

2. A 5β-hydroxy-Δ⁶-steroid of the formula

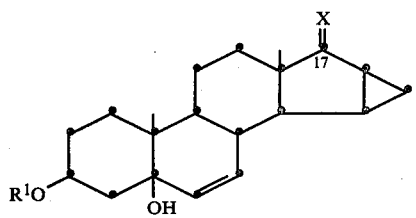

wherein
X is oxygen, or

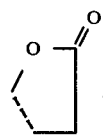

3. 3β-Acetoxy-5-hydroxy-15β,16β-methylene-5β-androst-6-en-17-one a compound of claim 2.

4. A process of claim 1, wherein the treatment temperature is 40°–70° C.

5. 3β,5-Dihydroxy-15β,16β-methylene-5β,17α-pregn-6-ene-21,17-carbolactone a compound of claim 2.

* * * * *